United States Patent [19]

Brandt et al.

[11] Patent Number: 5,135,924
[45] Date of Patent: Aug. 4, 1992

[54] THERAPEUTIC TREATMENT OF ANIMALS WITH ORAL ADMINISTRATION OF ORMETOPRIM-POTENTIATED SULFONAMIDES

[75] Inventors: Wallace E. Brandt, Kinnelon, N.J.; Lyle J. Hanson, Canon City, Colo.; Gianpaolo Maestrone, Staten Island, N.Y.

[73] Assignee: Hoffmann-La Roche Inc., Nutley, N.J.

[21] Appl. No.: 586,834

[22] Filed: Sep. 24, 1990

Related U.S. Application Data

[63] Continuation-in-part of Ser. No. 292,683, Jan. 3, 1989, abandoned, which is a continuation of Ser. No. 26,336, Mar. 16, 1987, abandoned.

[51] Int. Cl.$^5$ .............. H61K 31/635; H61K 31/505
[52] U.S. Cl. .................................. 514/157; 514/158; 514/275
[58] Field of Search .................. 514/157, 158, 275

[56] References Cited

U.S. PATENT DOCUMENTS

| | | | |
|---|---|---|---|
| 3,461,206 | 8/1969 | Hoffer et al. | 514/157 |
| 3,985,876 | 10/1976 | Hazlett et al. | 514/157 |
| 4,031,214 | 6/1977 | Easterbrook | 514/157 |
| 4,209,513 | 6/1980 | Torode et al. | 514/157 |

OTHER PUBLICATIONS

Can. J. Vet. Res. 1989:53:12–16 (1988).

*Primary Examiner*—Jerome D. Goldberg
*Attorney, Agent, or Firm*—George M. Gould; George W. Johnston; Alan P. Kass

[57] ABSTRACT

Systemic bacterial infections caused by aerobic and anaerobic organisms in companion animals such as dogs can be treated effectively and conveniently by the oral administration on a once a day basis of an antibacterial combination of ormetoprim and a sulfonamide, the activity of which is potentiated by ormetoprim. Various dosage forms are possible, including concentrates for addition to the feed or drinking water, as well as boluses, tablets, pastes, solutions, and suspensions for administration directly to the animals.

8 Claims, No Drawings

THERAPEUTIC TREATMENT OF ANIMALS WITH ORAL ADMINISTRATION OF ORMETOPRIM-POTENTIATED SULFONAMIDES

CROSS-REFERENCE TO RELATED APPLICATION

This application is a continuation-in-part application of Ser. No. 07/292,683, filed Jan. 3, 1989, now abandoned, which is a continuation of Ser. No. 07/026,336, filed Mar. 16, 1987, now abandoned.

BACKGROUND OF THE INVENTION

The present invention relates to the therapeutic treatment of systemic bacterial infections in non-human mammals by the oral administration on a once a day basis of ormetoprim-potentiated sulfonamides.

Modern methods of raising groups of farm animals and companion animals in confined areas enhance the incidence of microbial respiratory infection and other types of systemic infectious diseases. Such incidences vary from sporadic to enzootic, and the course of infection varies from acute to subacute to chronic. The outcome of the infection may be an uneventful recovery, but frequently severe weight loss, chronic disease conditions or death due to pathological changes in the animals may occur. Bacteria such as Hemophilus, Bordetella, Pasteurella, Staphylococcus, Salmonella, Klebsiella, Actinobacillus, Clostridium and other aerobic and anaerobic genera are usually isolated from clinical cases, implicating them in the causation of respiratory and other systemic diseases.

The health of farm and other animals can to an extent be regulated by the use of chemical and biological agents, which are injected into the animal or administered orally, for example, directly as a bolus or by addition to the feed or drinking water. Such agents include chemotherapeutic drugs for treating or preventing bacterial infections in animals and growth promoting additives for inclusion in livestock feed.

Diaminopyrimidine-potentiated sulfonamides are known to be useful as therapeutic or prophylactic agents in the control of diseases in animals. Such drugs are utilizable in turkey feed to prevent fowl cholera; see, for instance, Siegel et al., Avian Diseases, Volume 23, pages 409-416 (1979), and Olson, Poultry Science, Volume 56, pages 1098-1101 (1977). They are useful to treat coccidiosis, a parasitic infection in chickens; Orton et al., Poultry Science, Volume 50, pages 1341-1346 (1971). They have been studied as chemotherapeutic agents against Salmonella, Escherichia and Pasteurella in poultry; Mitrovic et al., Poultry Science, Volume 57, p. 1159 (1978), Olesiuk et al., Avian Diseases, Volume 17, pages 379-389 (1973); Sandhu et al., Poultry Science, Volume 59, pages 1027-1030 (1980). See also Havas et al., Chemotherapy, Volume 19, pages 179-195 (1973). It has also been revealed that the combination of sulfadimethoxine and ormetoprim is effective in pigs against localized digestive tract infections caused by *Escherichia coli*, Proceedings International Pig Vet. Soc., 1980 Congress, Copenhagen, Denmark; as well as *Sphaerophorus necrophorus*—induced experimental infections in mice, Maestrone et al., The Cornell Veterinarian, Volume 65, No. 2, pages 187-204 (1975). See also U.S. Pat. No. 3,461,206 to Hoffer et al. which disclose compositions of 2,4-diamino-5-(2',4',5-trisubstituted benzyl)pyrimidines and a sulfonamide as anticoccidial and antibacterial agents for poultry.

Diaminopyrimidine-potentiated sulfonamides have also been studied as chemotherapeutic agents against bacterial infections in horses; see, for instance, Adamson et al., Am. J. Vet. Res., Volume 46, pages 447-450 (1985); Brown et al., Am. J. Vet. Res., Volume 49, pages 918-922 (1988); and Brown et al., Am. J. Vet. Res., Volume 53, pages 12-16 (1989). Diaminopyrimidine-potentiated sulfonamides have also been studied as anticoccidiostats in dogs and coyotes. Dunbar et al., Am. J. Vet. Res., Volume 46, pages 1899-1902 (1985).

Injectable formulations of diaminopyrimidine-potentiated sulfonamides have been disclosed for the therapeutic treatment of bacterial infections in birds and mammals other than humans; U.S. Pat. No. 3,551,564 (Klaui et al.), U.S. Pat. No. 3,728,452 (Haber et al.), and U.S. Pat. No. 4,031,214 (Easterbrook et al.).

In addition, it has been established that potentiated sulfonamides promote growth in healthy farm animals, such as hogs, when added to the feed or drinking water; U.S. Pat. No. 3,715,433 (Bauernfeind et al).

SUMMARY OF THE INVENTION

The present invention relates to a method of therapeutically treating systemic bacterial infections in canines, comprising orally administering to the infected canine an effective amount of an antibacterial combination of sulfadimethoxine and ormetoprim in a weight ratio of sulfadimethoxine to ormetoprim of 5:1. Preferably, the antibacterial combination is administered on a once a day basis.

DETAILED DESCRIPTION OF THE INVENTION

The present invention is a method of therapeutically treating systemic (non-local) bacterial infections in mammals other than humans, comprising orally administering to the infected animal an effective amount of an antibacterial combination of ormetoprim and a sulfonamide. Ormetoprim is 2,4-diamino-5-(2'-methyl-4',5'-dimethoxybenzyl)pyrimidine.

The present invention relates to a method of therapeutically treating systemic bacterial infections in canines, comprising orally administering to the infected canine an effective amount of an antibacterial combination of sulfadimethoxine and ormetoprim in a weight ratio of sulfadimethoxine to ormetoprim of, 5:1. Preferably, the antibacterial combination is administered on a once a day basis.

The method can be used to treat companion animals, such as dogs. Types of systemic infections which commonly afflict such animals are septicemic, respiratory, soft tissue and urinary tract. Many anti-bacterial agents known to be useful against certain localized forms of infection, such as colibacillosis in pigs, are ineffective against systemic diseases. The present invention is based on the discovery, which was unexpected, that a once a day administration of ormetoprim-potentiated sulfonamides is useful to treat systemic infection when given orally and, moreover, is broadly effective against a wide variety of bacteria, including species which have developed resistance to sulfonamides and other conventional chemotherapeutic agents.

Suitable sulfonamides, for purposes of the present invention, are any of those which are effective in combatting aerobic and anaerobic bacterial infections in non-human mammals, are non-toxic to such mammals, and the anti-bacterial activity of which is enhanced by the presence of ormetoprim. Among those contemplated are sulfadimethoxine, sulfamethazine, sulfadiazine and sulfamethoxazol. Most especially preferred are combinations of ormetoprim and sulfadimethoxine.

The sulfonamide and ormetoprim can be employed in widely variant amounts relative to one another, especially 5:1.

For most infections, single daily doses in the range from 10 to 100 milligrams of antibacterial agent per kilogram of body weight of the animal being treated are sufficient. The time period for treatment will typically be from 3 to 20 days, depending on individual requirements.

Therapeutic treatment by the oral route in accordance with the present invention can be accomplished in any convenient manner. The active medicinal ingredients can be added in the form of a concentrate to the animals' feed or drinking water on a once a day basis. Alternatively, the active ingredients can be formulated into a once a day dosage in the form of a paste, bolus, tablet, solution or suspension using inert carrier materials and administered directly to the animal. Several suitable oral dosage forms for use in the practice of this invention are illustrated below.

It will be appreciated by those of ordinary skill in the art that various dosage forms can be formulated for each type of animal. In general, boluses are commonly used for bovines, pastes are commonly used for equines, solutions are commonly used for ovines, and tablets are commonly used for other animals, such as dogs. However, most any form of the combination can be given to most any animal.

ORAL DOSAGE FORM—BOLUS

Representative batch for 80,000 6.0 gram boluses:

| Ingredients | Amount |
| --- | --- |
| Sulfadimethoxine | 408.00 kg |
| Ormetoprim | 81.60 kg |
| Starch | 50.00 kg |
| Starch, direct compression grade | 28.00 kg |
| Pregelatinized starch | 30.00 kg |
| Coloring agent, Blue Lake #1, 13% | 0.40 kg |
| Sodium starch glycolate (modified starch) | 34.60 kg |
| Microcrystalline cellulose | 55.40 kg |

Procedure:
Form a powdered mixture of the above ingredients. Mill the powders, mix for 10 minutes, and granulate using about 500 milliliters of purified water per kilogram of milled powders. Mill the wet mass (optional). Dry the wet granulation product through a mill while adding 4.00 kg of magnesium stearate. Blend the milled granulation product in a mixture for 3 minutes, and compress into boluses.

Using the same amounts given above, the size of the bolus can be varied, for example, 1.2 g, 2.4 g, 12.0 g, and so forth, concomitantly also varying the total amount of boluses for the batch, for example, 400,000, 200,000, 40,000, and so forth.

If desired, the sodium starch glycolate and magnesium stearate can be omitted from this procedure.

ORAL DOSAGE FORM—PASTE (54%)

| Ingredients | Percent by weight |
| --- | --- |
| Sulfadimethoxine | 45.9 |
| Ormetoprim | 9.18 |
| Microcystalline wax | 3.0 |
| Silicon dioxide | 0.5 |
| Sorbic acid | 0.004 |
| Methyl paraben | 0.004 |
| Propyl paraben | 0.004 |
| Mineral oil | 41.408 |
| Total | 100.00 |

Procedure:
Add the microcrystalline wax and mineral oil to a suitable vessel. Heat the contents to 80° C., with mixing to melt the wax and dissolve the mineral oil in the melted wax. Add the sorbic acid, methyl paraben and propyl paraben (preservatives) and stir until dissolved. Add the silicon dioxide slowly with stirring until uniformly dispersed and thoroughly wetted. Add sulfadimethoxine and ormetoprim and continue stirring until a smooth, creamy paste is obtained. Fill the paste into syringe dispensing containers.

ORAL DOSAGE FORM—DRINKING WATER CONCENTRATE (3%)

| Ingredients | Amount |
| --- | --- |
| Sulfadimethoxine | 2.55 kilograms |
| Ormetoprim | 0.51 kilograms |
| Sodium hydroxide solution (4N) | 2.1 liters |
| Propylene glycol | q.s. |
| Total: | 100 liters |

Procedure:
Dissolve 400 grams of sodium hydroxide pellets in 1 liter of purified water in a stainless steel container. Add additional purified water to make 2½ liters, mix, and cool to room temperature. Add enough purified water to bring to a total volume of 2½ liters.

In separate glass-lined or stainless steel vessel over which a nitrogen blanket is supplied continously, add 95 liters of propylene glycol followed by 2.55 kilograms of sulfadimethoxine and mix to form a slurry. Add sufficient sodium hydroxide solution (see above) to adjust pH to 10.8±0.2 (diluted 1:1 with water). Add 0.51 kilograms of ormetoprim and continue stirring until dissolved. If desired, the mixture may be gently warmed, for example, to about 35°-50° C., to faciliatate dissolution. Allow the solution to stand overnight while maintaining the nitrogen blanket. Adjust the pH to 10.8±0.2, if necessary, with additional sodium hydroxide solution. Add sufficient propylene glycol to reach 100 liters and check final pH. Filter and fill into plastic bottles.

ORAL DOSAGE FORM—TABLETS

Representative batch for 4,000,000 tablets containing 100 mg. of sulfadimethoxine and 20 mg. of ormetoprim.

| Ingredients | Amount (kg) |
| --- | --- |
| Sulfadimethoxine | 408.00 |
| Ormetoprim | 81.60 |
| Starch | 50.00 |
| Starch, direct compression grade | 28.00 |
| Pregelatinized starch | 30.00 |

| Ingredients | Amount (kg) |
|---|---|
| FD&C Blue Lake #1, 13% | 0.40 |
| Sodium starch glycolate (modified starch) | 34.60 |
| Microcrystalline cellulose | 55.40 |

Procedure:

Blend the above ingredients to form a uniform mixture. The mixture is milled and then mixed for 10 minutes. Granulate the mixture using about 500 milliliters of purified water per kilogram of milled powder. Mill the wet mass (optional). Dry the wet granulation and pass the dried granulated material through a mill, adding 4 kilograms of magnesium stearate. Blend the milled granulation in a mixer for about 3 minutes and compress into tablets. If desired all or part of the sodium starch glycolate (modified starch) can be omitted from the granulation step and added together with magnesium stearate when the granulate is milled.

Those of ordinary skill in the art will realize that using the amounts above, the size of the tablets can be varied to increase the dosage of sulfadimethoxine and ormetoprim and, concomitantly, also varying the number of tablets made per batch.

Representative of the genera of bacteria known to cause systemic infection in mammalian animals, and for which the treatment method of the present invention is useful, are the following:

| | |
|---|---|
| Pasteurella | (for example, *multocida*) |
| Streptococcus | (for example, *agalactiae*) |
| Staphylococcus | (for example, *aureus*) |
| Salmonella | (for example, *typhimurium*) |
| Proteus | (for example, *vulgaris*) |
| Klebsiella | (for example, *pneumoniae*) |
| Clostridium | (for example, *septicum*) |
| Bordetella | (for example, *bronchiseptica*) |
| Actinobacillus | (for example, *lignieresi*) |
| Diplococcus | (for example, *pneumoniae*) |
| Hemophilus | (for example, *pleuropneumoniae*) |

The compositions of the present invention are particularly effective in the treatment of systemic infections in canines, bovines and equines and have effectiveness over a wide scope of genera of bacteria known to cause systemic infections in these animals.

Representative of the genera of bacteria known to cause systemic infections in canine animals, and for which the treatment method of the present invention is effective, include (representative species follow the genera): *Staphylococcus* (for example, *aureus* and *epidermidis*); *Streptococcus* (for example, *canis, equisimilis,* and *zooepidemicus*); *Acinetobacter* (for example, *calcoaceticus*); *Alcaligenes* (for example, *faecalis*); *Brucella* (for example, *canis*); *Escherichia* (for example, *coli*); *Klebsiella* (for example, *pneumoniae*); *Pasteurella* (for example, *multocida*); and *Proteus* (for example, *mirabilis* and *vulgaris*). Other representative genera include Bacillus, Corynebacterium, Enterobacter, Diplococcus, Enterococcus and Flavobacterium.

The usefulness of the present invention in the treatment of systemic infections in dogs is demonstrated by the in vivo tests described below.

UROGENITAL TRACT INFECTION—DOGS

The therapeutic effectiveness of 5:1 sulfadimethoxine/ormetoprim administered orally as tablets to dogs infected with urogenital tract bacterial infections was evaluated. Thirty-two cases were treated. Urogenital tract generally refers to those organs concerned with the production and excretion of urine together with the reproductive organs. Conditions treated included polyuria, incontinence, dysuria, hematuria, stranguria and prostatitis.

The medication was administered at a dose of 55 mg/kg body weight on the first day of treatment and 27.5 mg/kg daily on the subsequent days. Duration of the treatment ranged from 9 to 14 days. The results are summarized in Table 1. The dogs which recovered fully within one day from the systemic infection for which they were treated were rated "Excellent," those which recovered but more slowly, in three to four days, were rated "Good," and those which did not respond, no improvement after seven to ten days, were rated "No Effect."

TABLE 1

ORAL TREATMENT OF UROGENITAL TRACT INFECTIONS IN DOGS

| No. of Cases | Effect, % | | |
|---|---|---|---|
| | Excellent | Good | No Effect |
| 32 | 62.5 | 15.5 | 25.0 |

SOFT TISSUE INFECTION—DOGS

The therapeutic effectiveness of 5:1 sulfadimethoxine/ormetoprim administered orally as tablets to dogs with soft tissue infections of bacterial origin was evaluated. Conditions treated included infected bite wounds, post-surgical infections, abscesses, fistulas, anal sac infections, pyoderma, dermatitis, gingivitis, tonsillitis and pyometra. [the bacteria isolated from these lesions were identified and are listed as set forth hereinabove.]

The medication was administered at a dose of 55 mg/kg of body weight of the first day of treatment and at 27.5 mg/kg daily during the remainder of the treatment period. Duration of the treatment ranged from 5 to 11 days. The results were as follows:

TABLE 2

ORAL TREATMENT OF SOFT TISSUE INFECTION IN DOGS

| Infecting Bacterial Agent | No. Dogs Treated | % Improved |
|---|---|---|
| *Staph. aureus* | 22 | 100.00 |
| *E. coli* | 10 | 100.00 |
| Miscellaneous (42 species) | 77 | 98.7 |
| Totals: | 109 | 99.57 |

We claim:

1. A method of treating systemic bacterial infections in canines, comprising orally administering to the infected canine an antibacterially effective amount of a combination of sulfadimethoxine and ormetoprim in a weight ratio of sulfadimethoxine to ormetoprim of 5:1.

2. The method according to claim 1, in which the antibacterial combination is administered in the food or drinking water of the canine.

3. The method according to claim 1, in which the antibacterial combination is administered in the form selected from the group consisting of bolus, tablet, paste, solution, and suspension.

4. The method according to claim 3, in which the antibacterial combination is administered in the form of a tablet.

5. The method according to claim 4, in which the antibacterial combination is administered on a once a day basis.

6. The method according to claim 5, which is used to treat systemic bacterial infections selected from the group consisting of septicemic infections, respiratory infections, soft tissue infections, and urogenital tract infections.

7. The method according to claim 6, wherein the systemic bacterial infection is caused by one or more bacteria selected from the genera group consisting of Staphylococcus, Streptococcus, Acinetobacter, Alcaligenes, Brucella, Escherichia, Klebsiella, Pasteurella, Proteus, Bacillus, Corynebacterium, Diplococcus, Enterobacter, and Enterococcus.

8. The method according to claim 5, in which the antibacterial combination is administered at a dose of from about 10 milligrams to about 100 milligrams per kilogram of canine body weight.

* * * * *